US012629434B2

(12) United States Patent
Ciesiun

(10) Patent No.: US 12,629,434 B2
(45) Date of Patent: May 19, 2026

(54) ULTRAVIOLET LIGHT GERMICIDAL IRRADIATION DEVICE

(71) Applicant: Paul M. Ciesiun, Mokena, IL (US)

(72) Inventor: Paul M. Ciesiun, Mokena, IL (US)

( * ) Notice: Subject to any disclaimer, the term of this patent is extended or adjusted under 35 U.S.C. 154(b) by 990 days.

(21) Appl. No.: 17/087,507

(22) Filed: Nov. 2, 2020

(65) Prior Publication Data

US 2021/0316022 A1    Oct. 14, 2021

Related U.S. Application Data

(60) Provisional application No. 63/009,896, filed on Apr. 14, 2020, provisional application No. 63/006,904, filed on Apr. 8, 2020.

(51) Int. Cl.
A61L 2/10 (2026.01)
A61L 103/00 (2026.01)

(52) U.S. Cl.
CPC ............. A61L 2/10 (2013.01); A61L 2103/00 (2026.01); A61L 2202/11 (2013.01)

(58) Field of Classification Search
CPC .... A61L 2/10; A61L 2202/11; A61L 2202/20; A61L 2202/14
See application file for complete search history.

(56) References Cited

U.S. PATENT DOCUMENTS

2007/0299558 A1*  12/2007  Nelson ................. H05B 3/0052
                                                        700/259
2010/0102252 A1*   4/2010  Harmon ................... A61L 2/10
                                                        250/492.1

2011/0305597 A1*  12/2011  Farren ....................... A61L 2/10
                                                        422/24
2014/0330452 A1*  11/2014  Stewart .................... B25J 19/02
                                                        701/2
2016/0213798 A1*   7/2016  Paver, Jr. .................. A61L 2/22
2016/0271803 A1*   9/2016  Stewart ............... B25J 11/0085
2018/0207303 A1*   7/2018  Farren ....................... A61L 2/04
2019/0317383 A1*  10/2019  Llewelyn-Davies .. H04N 23/54
2020/0085983 A1*   3/2020  Ramanand ................. A61L 2/10
2020/0178760 A1*   6/2020  Kashima ........... A61B 1/00188
2020/0205609 A1*   7/2020  Hood ................... C12Q 1/6869
2020/0230273 A1*   7/2020  Farren ................... H01J 37/244

FOREIGN PATENT DOCUMENTS

WO        WO-2021178782 A1 *  9/2021  ............... A61L 2/10

* cited by examiner

*Primary Examiner* — Regina M Yoo
(74) *Attorney, Agent, or Firm* — Donald G. Flaynik

(57) ABSTRACT

An ultraviolet light germicidal irradiation device includes a base member having a mounting plate for detachably securing the base member to a selected surface; an extension member detachably and substantially vertically secured to the base member; an arm member rotationally secured to the extension member, whereby, a top portion of the arm member is disposed outside the periphery of either side of an object to be decontaminated; an ultraviolet light housing pivotally secured to the top portion of the arm member, whereby, a front portion of the ultraviolet light housing has a pivoting range from at least twenty degrees above a horizontal plane to forty degrees below the horizontal plane; and an ultraviolet light lamp disposed inside the ultraviolet light housing, the ultraviolet light lamp emitting an ultraviolet light at a preselected wave length that destroys a preselected virus without injuring humans.

20 Claims, 14 Drawing Sheets

ULTRAVIOLET LIGHT GERMICIDAL IRRADIATION DEVICE

This Utility Application is based on Provisional Patent Application No. 63/006,904 filed Apr. 8, 2020 and Provisional Patent Application No. 63/009,896 filed Apr. 14, 2020.

BACKGROUND OF THE INVENTION

1. Field of the Invention

The present invention relates to a Device for decontaminating and disinfecting packages and other objects that could be infected with contagious pathogens. The device and process for decontaminating and disinfecting a selected object includes exposing the object to ultraviolet light for a predetermined time that destroys anticipated contagious pathogens. The present invention includes control circuits for energizing and de-energizing one or more ultraviolet light members, whereby, persons are not exposed to ultraviolet light when objects are decontaminated and disinfected via ultraviolet light engulfing the objects. In particular, the present invention relates to disinfecting a keypad for a credit/debit card "reading" device.

2. Background of the Prior Art

The present health environment is dominated by daily news of person infected by Covid-19 Virus, or have died as a result of being infected with Covid-19 virus. In March 2020 the Center for Disease Control found that the Covid-19 virus had been discovered on surfaces of the Diamond Princess Cruise Ship 17 days after passengers departed. The covid-19 was still contagious and required mitigation in order to prevent further spread of the disease.

Not only is the Covid-19 Virus problematic for surfaces in ocean vessels, the virus also "attaches" to packages enclosing manufactured goods, resulting in a relatively simple method to spread the virus. For example, Amazon delivered nearly 3.5 billion packages in 2019 as a result of online purchases. These packages are then delivered to homes and businesses in a short time frame, often the next day. Purchases are often picked, packed and shipped from a central distribution point, but are often handled by multiple persons. This creates a prime opportunity for a highly contagious pathogen to spread relatively fast across a relatively large geographical area. To mitigate the risk of spreading the virus, it is highly desirable to "sanitize" the exterior of these packages to make the packages safe for purchasers lifting or otherwise engaging packages brought into purchaser's homes and/or businesses.

For nearly 100 years, it has been known that ultraviolet ("UV") light is a highly effective germicide. UV light generated by the sun is capable of rendering pathogens inert via a photochemical reaction which produces a "molecular lesion" known as a pyrimidine dimer in thymine (DNA) or Uracil (RNA) and which results in a nucleotide strand, but ultimately disrupts the sequence and prevents replication of the pathogen. In particular, recent studies have shown specific wavelengths of UV light (200-300 nm) are highly effective against these pathogens, and UV light between 207 and 222 nm have been found to efficiently kill bacteria and viruses without causing damage to human cells.

Prior art UV light generating devices for sterilizing purposes are well known and include but not limited to equipment for sterilizing, for example: air in an enclosure (U.S.

Pat. No. 9,457,121), perishable food items in an enclosure (U.S. Pat. No. 9,179,703), skin disorders using a hand held UV light generating device (U.S. Pat. No. 9,162,078), and items in a drawer in an enclosure (U.S. Pat. No. 9,024,277). None of the prior art provides a UV light generating device that disinfects a financial scanning or reading device for credit/debit cards, whereby, the device is disposed upon a checkout counter and the users of the device being routinely exposed to the UV light.

A need exists for an ultraviolet light germicidal irradiation device that incorporates features that destroy viruses present on packages and/or financial transactions devices having varying configurations (in particular, a credit/debit card reading device) without using an enclosure and without injuring persons routinely exposed to the ultraviolet light.

SUMMARY OF THE INVENTION

It is an object of the present invention to provide a device for decontaminating and disinfecting objects from contagious pathogens by engulfing the objects with ultraviolet light ("UV") emitted from a UV lamp positioned proximate to the objects. It is a primary object of the present invention to provide a device that emits UV light that is non-harmful to human skin and eyes. A feature of the device is a UV lamp technology that emits between 207 and 222 nanometer ("nm") UV light that is non-harmful to human skin and eyes. Another feature of the device is a "Far UVC light" (a preferred UV light) having a krypton-chlorine Excimer Lamp that emits monoenergetic UV light at substantially a wavelength of 222 nanometers. An advantage of the device is that the UV lamp does not have to be de-energized to maintain human safety. Another advantage of the device is that the preferred UV light device inactivates a contagious virus but is not cytotoxic or mutagenic to mammalian cells. Still another advantage of the device is that the preferred UV light device decontaminates surfaces engaged by humans, surfaces previously engaged by humans or within a predetermined space occupied by humans, whereby, a person or persons exposed to the UV light generated by the UV lamp is not harmed.

Another object of the present invention is to provide a UV device that decontaminates and disinfects a keypad device used for financial transactions including but not limited to credit card purchases in high traffic areas. A feature of the UV device is a UV lamp that is adjustably positioned, whereby, the UV lamp is disposed between three to seven inches from the surface of the keypad device. Another feature of the UV device is that the device can be programmed to have a time value setting (lamp on) based light intensity (lamp power and UV wavelength) and the distance to a surface or area to be irradiated. An advantage of the device is that by disposing the UV lamp between three to seven inches from the surface of the keypad device, maximum disinfection is achieved during a minimum time parameter. Another advantage of the UV device is that in the event that the surface of the keypad device (or other object) is separated from the UV lamp a distance greater than seven inches, the UV lamp can be programmed to remain energized for a time period required to disinfect the surface of the keypad device based on the distance of separation between the keypad surface and the UV lamp.

Still another object of the present invention is to provide a UV device that allows the UV lamp to be manually re-positioned to allow relatively easy access to the keypad device. A feature of the UV device is a manually rotatable UV lamp housing that re-positions from a maintained location directly above the keypad device to a ninety degree rotated "locked" location distal to a selected side of the keypad device, whereby, the entire surface of the keypad device is viewable by a user of the keypad device and the UV lamp is automatically de-energized. Another feature of the UV device is that the UV lamp housing is manually "unlocked" from a selected side of the keypad device, then manually rotated back to the location directly above the keypad device, whereby, the UV lamp is automatically re-energized. An advantage of re-positioning the UV lamp housing to the either side of the keypad device is that a purchaser can with relative ease insert a credit/debit card into the keypad device without exposure to UV light. Another advantage of the rotated locked location of the UV lamp housing is that by automatically de-energizing the UV lamp, a user of the keypad device need not be concerned about possible harmful effects from an energized UV lamp, irrespective of the UV lamp generating UV light at 222 nm, which is not harmful to humans or test animals.

Yet another object of the present invention is to provide a UV lamp housing that pivots from a front position ranging from twenty degrees above a horizontal plane down to a front position forty degrees below a horizontal plane. A feature of the UV lamp housing is a constant torque hinge that holds the position of the UV lamp housing at any front position within the sixty-degree front position range. An advantage of the UV device is that the adjustable front positioning of the UV lamp promotes a distance of separation between the UV lamp and the keypad device within the range of three to seven inches, thereby achieving maximum disinfection of the surface of the keypad device.

Another object of the present invention is to provide a UV lamp housing having power, reset and cycle duration controls. A feature of the UV device is an on-off power switch, a cycle reset switch for restarting a cycle duration time, and a three-position cycle duration switch for selecting one of three cycle duration times for the UV lamp to emit UV light for irradiating the keypad device. An advantage of the UV device is that when the UV lamp housing is vertically adjusted within the three to seven-inch front position range, the cycle duration time for the UV lamp can be correspondingly adjusted from a minimum exposure time for three inches of separation to a maximum exposure time for seven inches of separation.

Another object of the present invention is to provide a UV lamp housing having indicators informing a person using the UV device as to the status of the irradiation cycle remaining for the UV lamp. A feature of the UV device is three colored lights, red representing the start of the irradiation cycle, yellow representing a mid-portion of the irradiation cycle, and purple representing the completion of the irradiation cycle. Another feature of the UV device is that if the UV lamp housing is left in a vertical position after the irradiation cycle is complete, the purple light pulses and fades until the UV lamp housing is rotated to a side position relative to the keypad device or the cycle reset switch is pressed. An advantage of the UV device is that the colored lights provide an estimate as to the remaining irradiation time, thereby avoiding the user from losing focus on the UV device. Another advantage of the UV device is that the pulsating purple light announces to the user of the keypad device that the transaction is complete, thereby reducing the time that a purchaser delays removing their credit card from the keypad device, resulting in more financial transactions in a respective time period.

Other features and advantages of the present invention include:

Proximity sensors (well known to those or ordinary skill in the art) for turning off the UV lamp in the event a person places their hand under the lamp when energized and irradiating a surface of an object including a keypad;

Multiple time settings for varying UV dosage (dosage=UV light intensity (lamp power and UV frequency)×time) based upon the time of year. The colder the temperature, the greater the dosage upon the surface of the keypad or object.

The UV device can be portable or secured to a surface.

The UV device includes a lamp life estimated at 3,000 hours.

The UV device can be powered via a 120 VAC or 12 VDC that provides 24 watts.

BRIEF DESCRIPTION OF THE DRAWINGS

The foregoing invention and its advantages may be readily appreciated from the following detailed description of the preferred embodiment, when read in conjunction with the accompanying drawings in which.

DESCRIPTION OF THE PREFERRED EMBODIMENT

Figure 1:
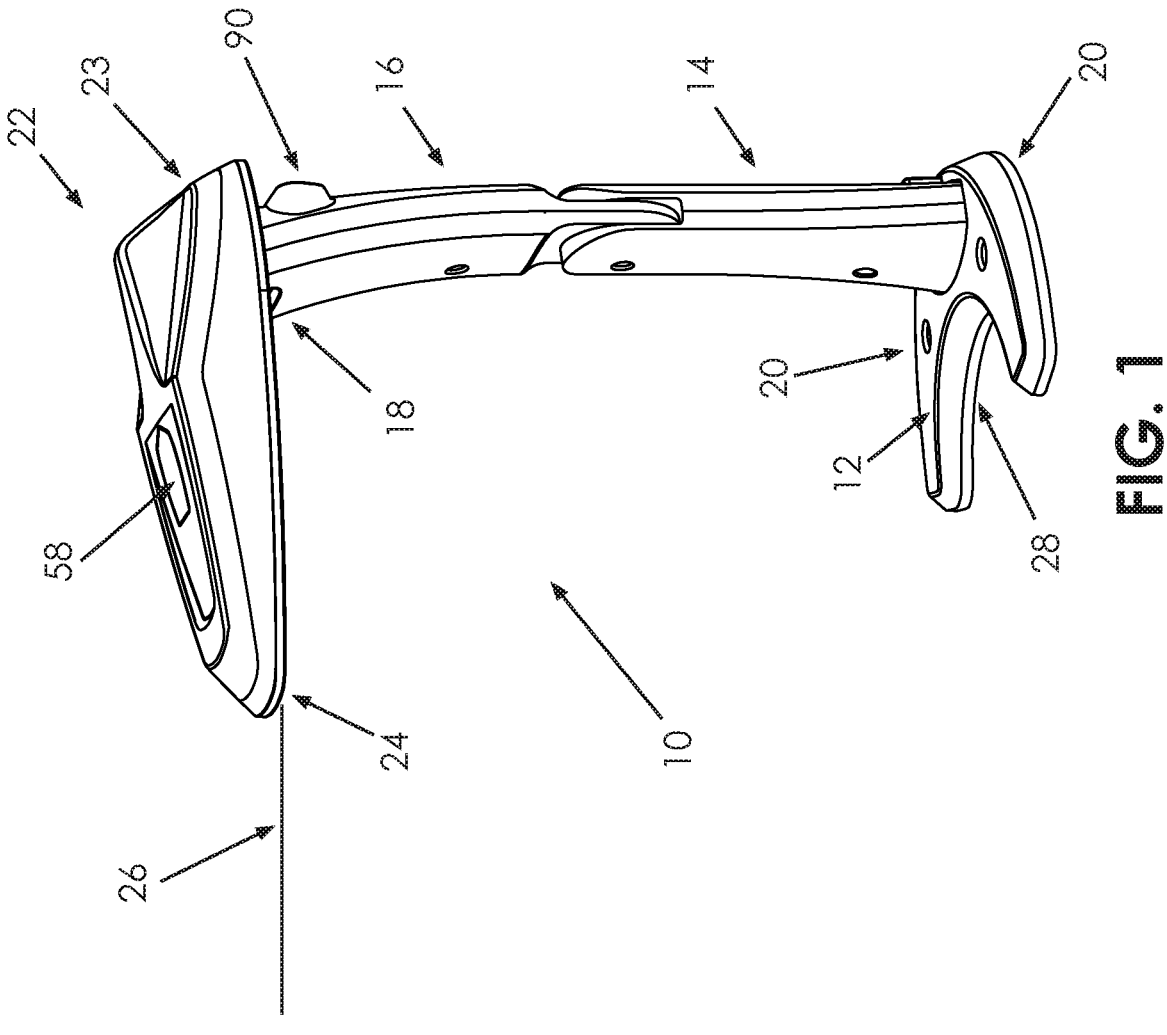
FIG. 1 is a side perspective view of an ultraviolet light ("UV") germicidal irradiation device in accordance with the present invention.

Referring to figures, an ultraviolet light ("UV) germicidal irradiation device in accordance with the present invention is denoted as numeral 10. The device 10 includes a base member 12 having a substantially perpendicular extension member 14 detachably secured to the base member 12; an arm member 16 rotationally secured to the extension member 14, whereby, a top portion 18 of the arm member 16 can be disposed outside the periphery of either side of an object to be decontaminated; and a UV housing 22 having a back portion 23 pivotally secured to the top portion 18 of the arm member 16, whereby, a front portion 24 of the UV housing 22 has a pivoting range from at least twenty degrees 25 (FIG. 10) above a horizontal plane 26 to at least forty degrees 27 (FIG. 11) below the horizontal plane 26. The extension member 14 and arm member 16 are substantially vertically aligned, whereby, the front portion 24 of the UV housing is disposed above an object to be irradiated with UV light. The UV housing 22 includes a configuration, when taking a top view of the device 10, having a longitudinal dimension relatively larger than a lateral dimension of the housing 22, thereby distally disposing a UV lamp 38 from the arm member 16 for promoting UV light emission upon the object to be decontaminated.

Figure 8:
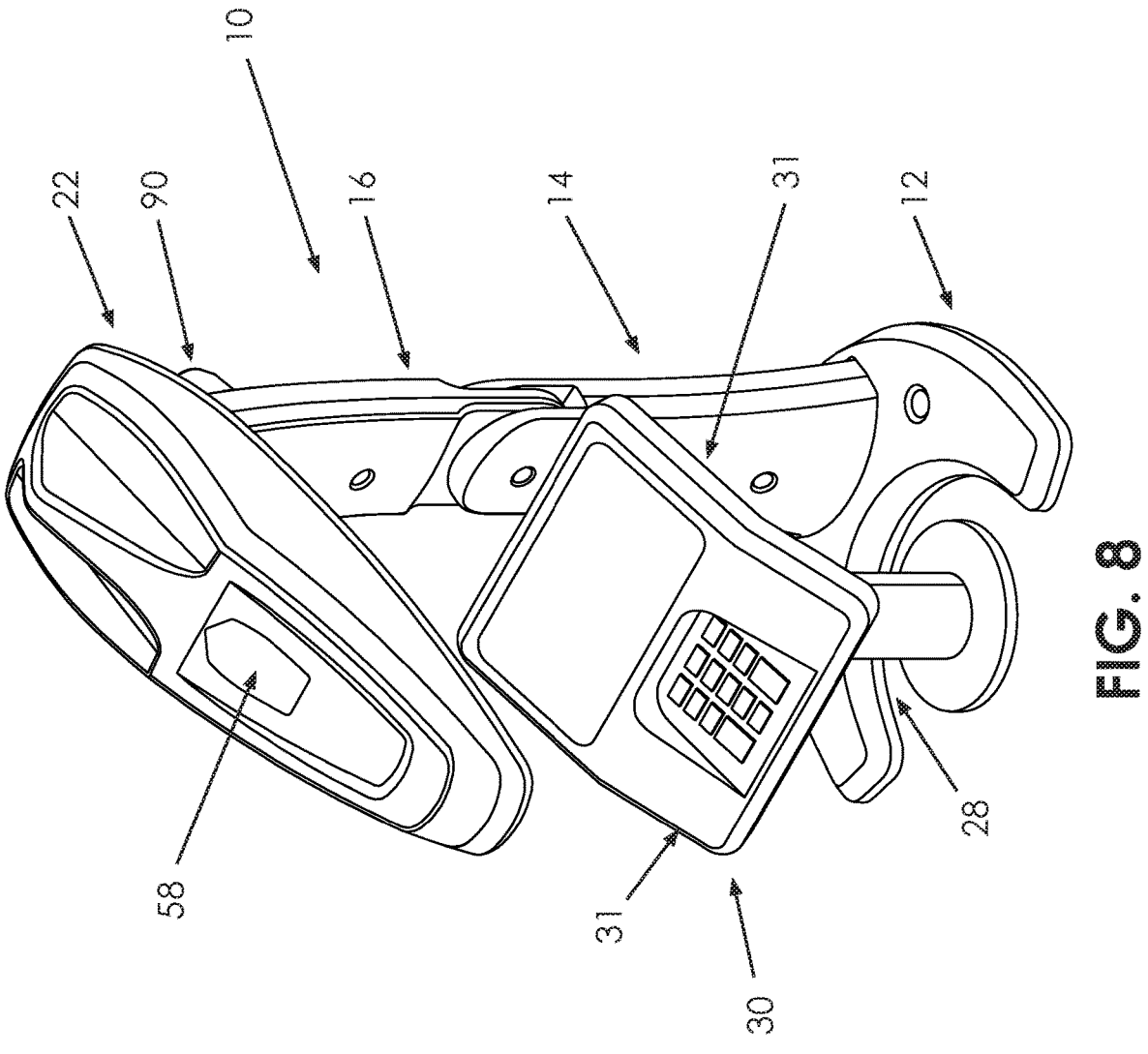
FIG. 8 is the front perspective view of FIG. 3, but with a keypad device disposed proximate to and detached from a base portion of the device of FIG. 1.
Figure 9:
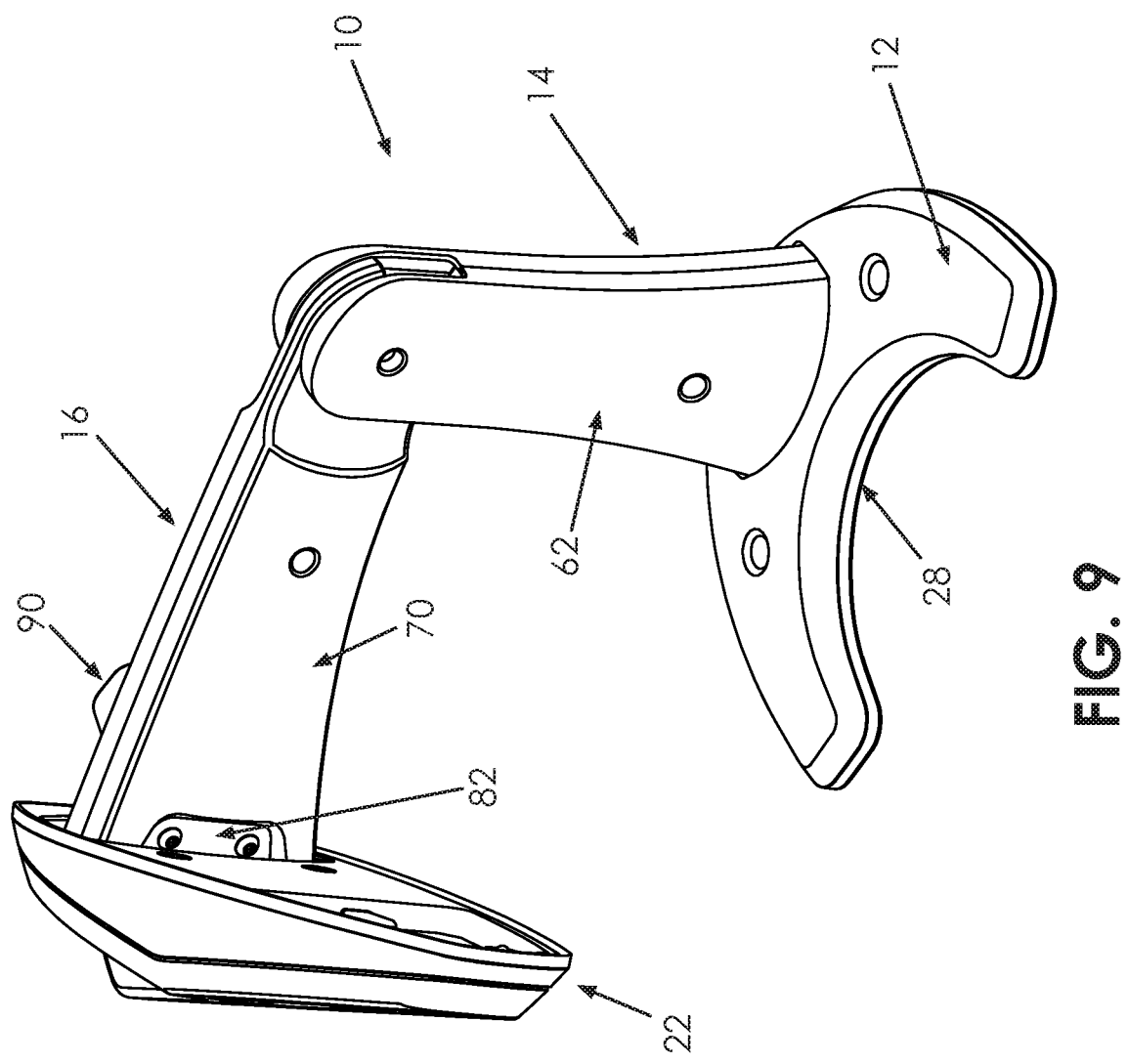
FIG. 9 is the front perspective view of FIG. 3, but with an ultraviolet light lamp housing disposed in a rotated position to the left side of the base member of the UV device.

The base member 12 can be fabricated from plastic, metal or similar rigid materials and includes a recess 28 for receiving an object and in particular a keypad device 30 (FIG. 8) for decontamination, whereby, the keypad device 30 (not part of the present invention) is disposed beneath the UV housing 22 for receiving UV light that decontaminates and disinfects the keypad device 30 of anticipated contagious pathogens including the covid-19 virus. The base member 12 further includes a mounting plate 32 for detachably securing the UV germicidal irradiation device 10 to a counter top or similar surface for conducting financial transactions via a keypad device 30 or for engulfing packages with UV light before delivery to a predetermined destination. Although the base member 12 has been described as having a recess 28, which is the preferred configuration, the base can have a myriad of configurations and dimensions that can cooperate with the keypad device 30, whereby, the keypad device 30 is disposed beneath UV light for decontamination.

Referring to FIGS. 1-28, the UV housing 22 can be fabricated from plastic, metal or similar rigid materials and is formed from lower and upper hood portions 34 and 36. The UV housing 22 encloses a compression bracket 44 securing a UV lamp 38 below a reflector 40 and above a UV light filter 42 that covers an aperture 43 in a front portion 46 of the lower hood 34. The reflector 40 is a high reflective PTFE sheet of material manufactured by ThorLabs, item #PLMR10P1. The UV housing 22 further includes a ballast board 48 manufactured by Eden Park, model #EPI 10W Ballast V0.2a. The ballast board 48 is secured to a mid-portion of the lower hood portion 34. The ballast board 48 "steps-up" the voltage supplied by a typical 120 VAC power cord (not depicted) to a magnitude that results in the UV lamp 38 emitting a UV light having a wavelength between 201 and 222 nanometers ("nm") after the emitted UV light is filtered via an Omega Optical, LLC filter (type MDM & Dielectric SP filter) 42.

Figure 10:
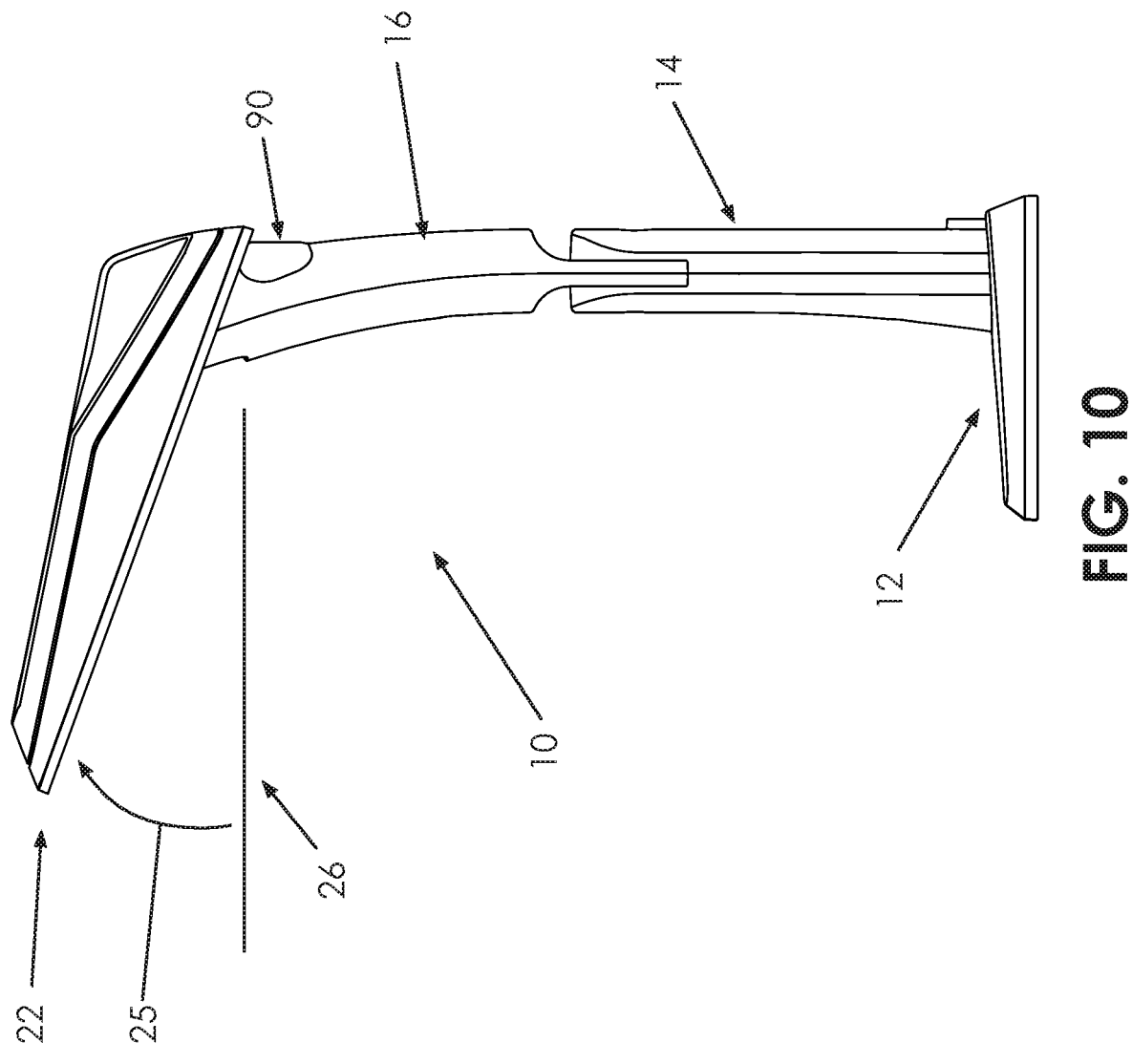
FIG. 10 is the right side elevation view of the device of FIG. 6, but with the UV lamp housing disposed in a front position twenty degrees above horizontal.
Figure 11:
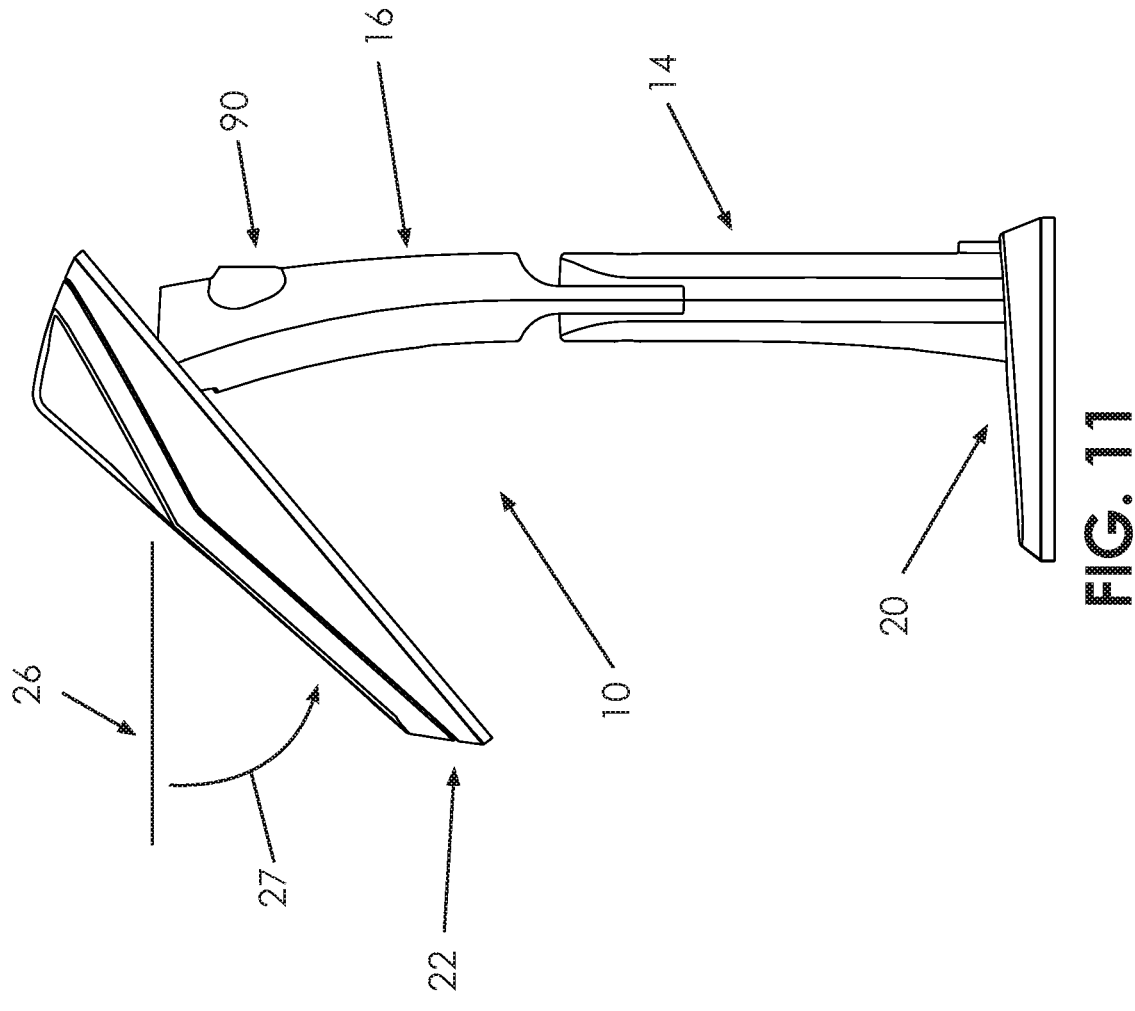
FIG. 11 is the right side elevation view of the device of FIG. 6, but with the UV lamp housing disposed in a front position forty degrees below horizontal.

An aperture 50 in a back portion 52 of the lower hood 34 removably receives a back upper portion 54 of the arm member 16 when the front portion 46 of UV housing 22 is disposed above (as much as twenty degrees) the horizontal plane 26 that intersects the top portion 18 of the arm member 16 (see FIG. 10). The upper hood portion 36 of the UV housing 22 includes an aperture 56 that removably receives a logo lens 58 illuminated and detachably secured to an inner surface of the upper hood 36 via a light emitting diode ("LED") circuit board 60 detachably secured to an inner surface of the upper hood 36. The LED circuit board 60 includes first, second and third LEDs 91. The first LED manufactured by Vishay Lite-on having part number LTST- C191KGKT emits a green light viewable through the logo lens 58 and aperture 56 representing a power-on status for the device 10. The second LED manufactured by Lumex Opto/Components, Inc. having part number SSL-LX5093VC emits a purple light viewable through the logo lens 58 and aperture 56 representing that the UV lamp 38 is energized and irradiating. The third LED light manufactured by Kingbright having part number WP710A10ZGC/G emits a red light viewable through the logo lens 58 and aperture 56 representing that the device has completed an irradiation cycle and that the device is ready for another financial transaction. Alternatively, the third LED light emits a yellow light representing a "Fault" condition or that the device 10 is in a stow position and that the device 10 requires the attention of the user of the device 10 to correct the problem.

Figure 2:
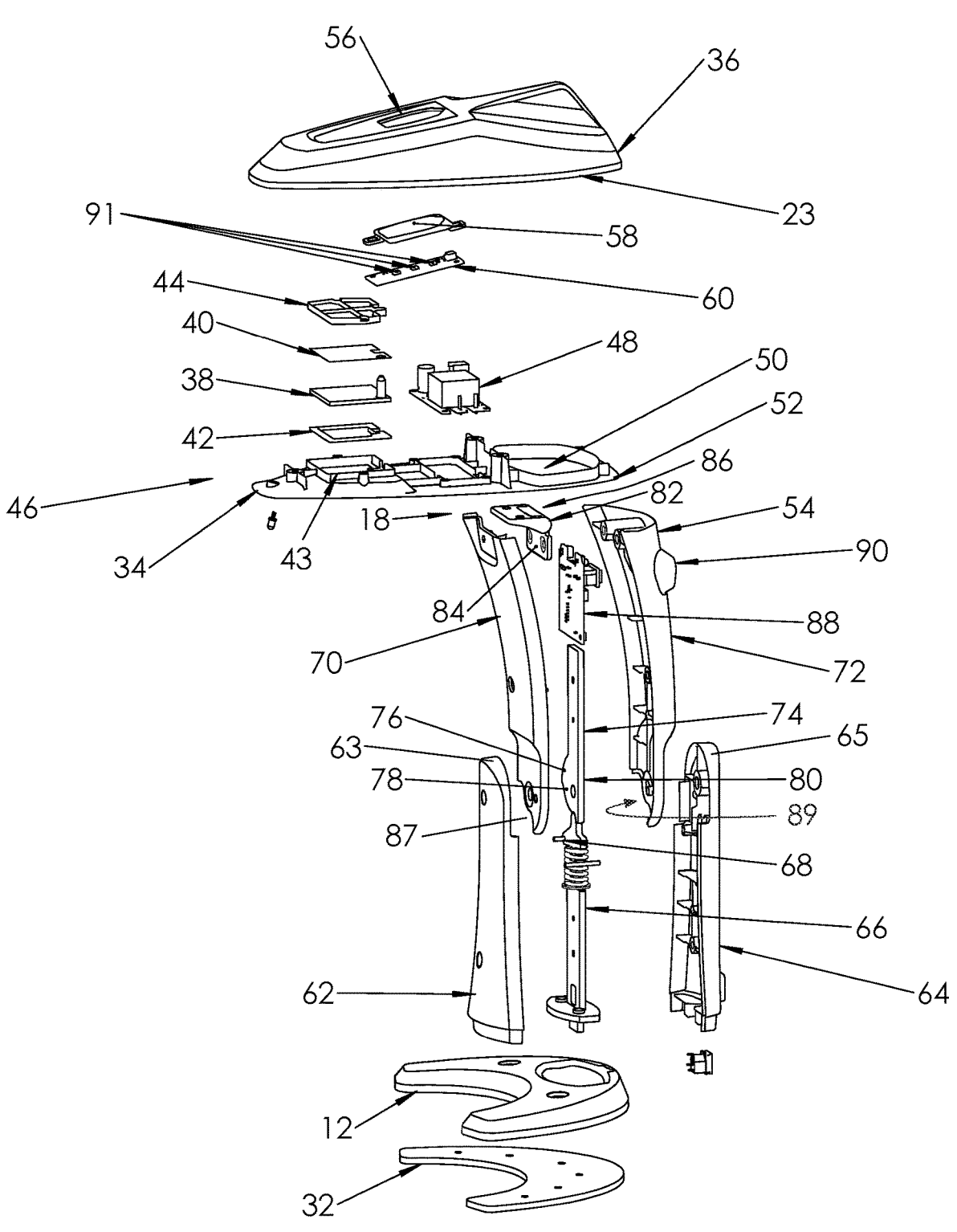
FIG. 2 is an exploded view of the UV device in FIG. 1.
Figure 2A:
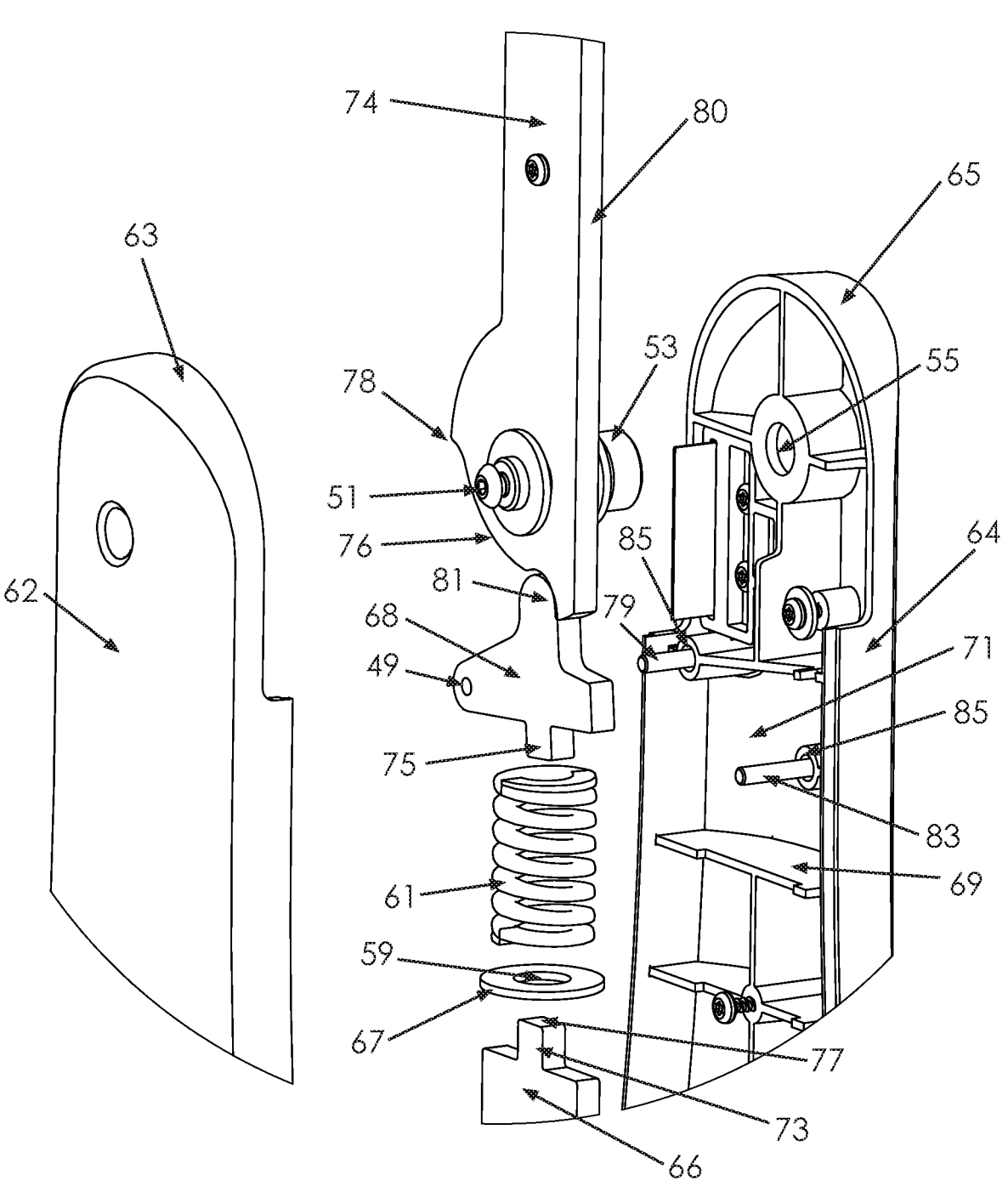
FIG. 2A is an exploded perspective view of rotatable portions of the extension and arm members depicted in FIGS. 1 and 2 in accordance with the present invention.
Figure 2B:
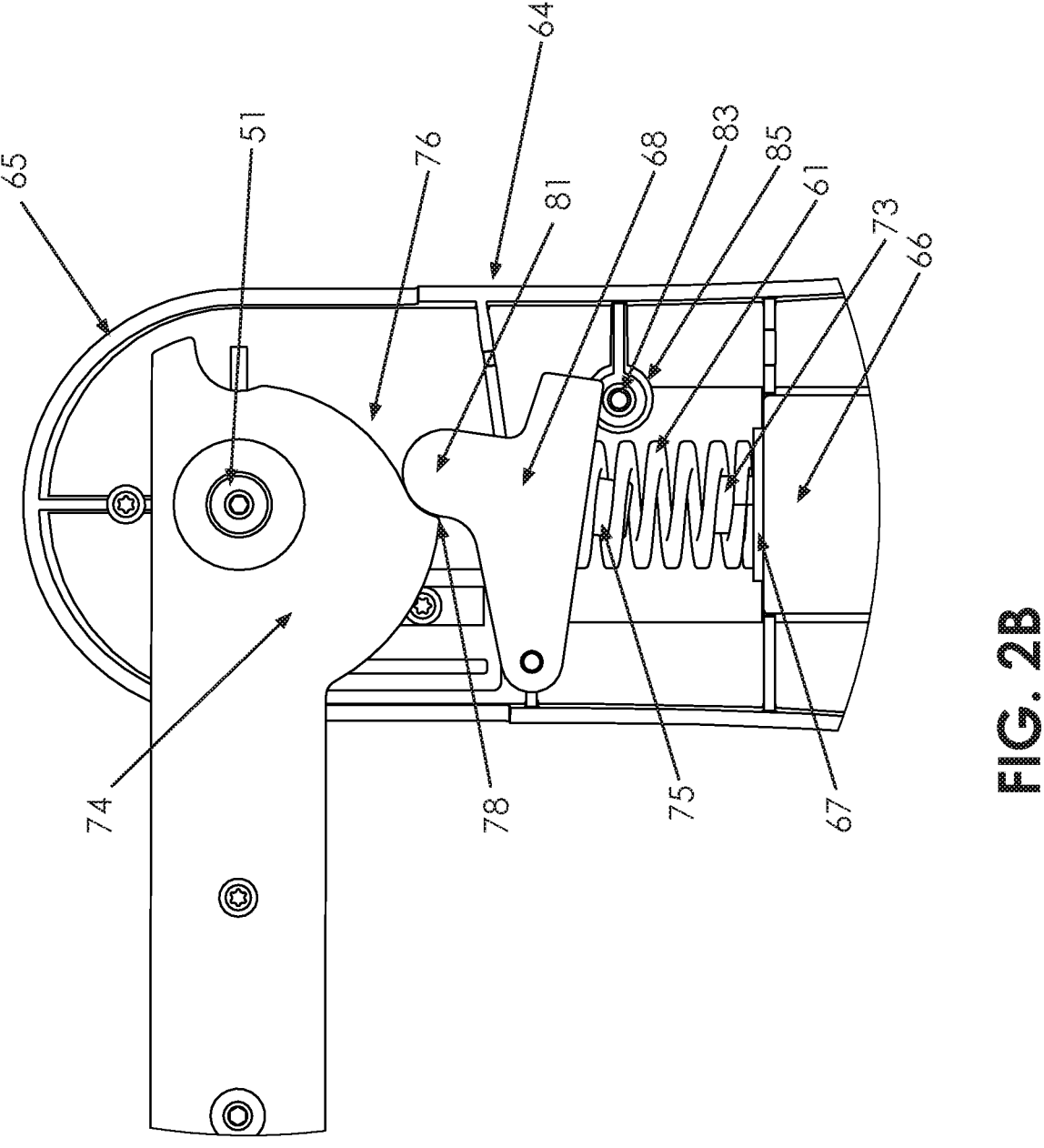
FIG. 2B is a front perspective view of the internal rotational components of FIG. 2A disposed in a rotated position.

Referring to FIGS. 2, 2A and 2B, the extension member 14 can be fabricated from plastic, metal or similar rigid materials and includes front and back covers 62 and 64 detachably joined together, via fasteners well known to those of ordinary skill in the art, to encase a bracket plate 66 having a top protrusion portion 73 that extends through an aperture 59 in a spring retainer washer 67 and into a bottom portion of a spring 61 engaging and disposed between the spring retainer washer 67 and a cam member 68. The bracket plate 66 is captured inside the detachably joined front and back covers 62 and 64 via retaining trays 69 laterally and integrally joined to inner walls 71 of the back covers 62 and 64.

The cam member 68 includes a spring retainer portion 75 that extends into a top center portion of the spring 61 a distance that promotes engagement of a bottom portion of the cam member 68 with a top portion of the spring 61 (see FIG. 2A). When the arm member 16 is substantially lineally aligned with the extension member 14, a bottom of the cam member 68 and spring retainer portion 75 cooperate with the top protrusion portion 73 of the bracket plate 66 and the spring retainer washer 67 to capture and slightly compress the spring 61, thereby maintaining the spring 61 in a slightly biased condition and removing any dead band from the spring 61 before the spring 61 is compressed via rotation of the cam plate 74. When the arm member 16 is rotated ultimately ninety degrees relative to the extension member 14, (see FIG. 9), the spring retaining portion 75 and the bottom of the cam member 68 cooperate to compress the spring 61 against the spring retainer washer 67 until the cam member 68 is angularly positioned via the axial location of a first retaining pin 79 inserted through the cam member 68, and the axial location of a second retaining pin 83 engaging the bottom portion of the cam member 68 (see FIGS. 2A and 2B).

A first retaining pin 79 inserts through the cam member 68 via an aperture 49 and into a receiving recess 85 in the back cover 64, thereby substantially maintaining the position of the cam member 68 relative to the lower portion 76 of the cam plate 74 as the cam plate 74 is rotated from vertical to rotated positions and back to a vertical position. Further, the first retaining pin 79 inserts into a receiving recess (not depicted) in the front cover 62 when the front and back covers are detachably joined, thereby maintaining the axis of the pin 79 in a substantially horizontal position, irrespective of the force generated upon the pin 79 by the rotational motion of the lower portion 76 upon the tip portion 81. The first retaining pin 79 and the spring 61 cooperate to substantially maintain the position of the cam member 68 throughout the rotational movement of the lower portion 76 with the exception of a relatively slight angular position determined by the axial location of the first retaining pin 79 and axial location of a second retaining pin 83 engaging a corresponding bottom portion of the cam member 68. The second retaining pin 83 is inserted into and maintained in a receiving recess 85 in the back cover 64. The second retaining pin 83 stops the rotation of the cam member 68 via the first retaining pin 79, thereby limiting the rotational movement of the lower portion 76 of the cam plate 74 upon the tip portion 81 of the cam member 68, resulting in the positioning of the arm member 16 at substantially ninety degrees relative to the extension member 14 (see FIGS. 1 and 9).

The arm member 16 includes front and back covers 70 and 72 having respective lower end portions 87 and 89 rotationally and detachably secured to respective upper end portions 63 and 65 of front and back covers 62 and 64 of the extension member 14. The Joined front and back covers 70 and 72 of the arm member 16 encase a cam plate 74 having a lower portion configured to cooperatively engage the cam member 68 of the bracket plate assembly 66 with the spring 61 not compressed between the spring retainer 67 and cam member 68. When the arm member 16 is forcibly rotated to a de-energized position (substantially ninety degrees relative to the extension member 14) via a first bushing 51 rotatably inserted into a first bushing retainer (not depicted) in the front cover 62 and a second bushing 53 inserted in a second bushing retainer 55 in the back cover 64. The configuration of the lower portion 76 of the cam plate 74 urges the cam member 68 downward, thereby compressing the spring 61 and maintaining the rotated position of the arm member 16 via a relatively "pointed" protrusion portion 78 on the lower portion 76 engaging a "tip" portion 81 of the cam member 68. When the rotated arm member 16 is to be returned to an energized or vertical position, the compressed spring 61 imparts a force that assists the user when manually rotating the arm member 16 to substantially vertical position to disinfect a keypad device 30.

Although FIGS. 2, 2A and 2B depict the configuration of the lower portion 76 of the cam plate 74 with only the left side of the cam plate 74 promoting rotation of the arm member 16, the bracket plate 66 and cam plate 74 can be rotated one hundred and eighty degrees, whereby, the lower and protrusion portions 76 and 78 of the cam plate 74 are disposed to promote rotation of the arm member 16 on the right side of the extension member 14. The vertical/longitudinal dimensions of the extension member 14 and arm member 16 cooperate, whereby, the UV housing 22 is disposed above the keypad device 30 a preselected distance and the top portion 18 of the arm member 16 is disposed outside the periphery of either side 31 of the keypad device 30 when the arm member 16 is rotated substantially ninety-degrees from a vertical position.

The ninety-degree rotation of the UV housing 22 from a position above a keypad device 30 to a maintained position outside the periphery of the base member 12 allows relatively easy access to the keyboard device 30 by a person initiating a financial transaction by inserting a debit or credit card into the keyboard device 30. Further, after rotating the UV housing 22, the entire surface of the keypad device 30 is viewable by a user of the keypad device 30, and the UV lamp 38 is automatically de-energized by an electrical limit switch (not depicted but well known to those of ordinary skill in the art) in the electrical circuit supplying 120 V.A.C. power to the ballast board 48. The UV housing 22 is manually urged from the rotated position at a selected side of the keypad device 30 to a position directly above the keypad device 30, whereupon, the UV lamp 38 is enabled to be re-energized via an electrical gyro switch 94 in series with a reset pushbutton switch 92, thereby minimizing "down time" for the keypad device 30 and increasing the number of financial transactions in a given time period. The de-energizing of the UV lamp 38 enables a user to insert credit/debit card into the keypad device 30 without exposure to UV light generated by the UV lap 38, resulting in a user of the keypad device 30 not being concerned about possible harmful effects from an energized UV lamp 38, irrespective of the UV lamp 38 generating UV light at 222 nm, which is not harmful to humans or test animals.

A constant torque hinge 82 manufactured by Southco External Hinges having part #E6-10-430-50 includes a lower vertical portion 84 detachably secured inside a top portion 18 of the arm member 16, and further includes an upper horizontal portion 86 detachably secured to the lower hood 34 of the UV housing 22 adjacent to the aperture 50. The constant torque hinge 82 and aperture 50 enable the UV housing 22 to be manually positioned to maintained upper and lower locations, whereby, the front portion 46 of the UV housing 22 is pivoted up to twenty degrees above the horizontal plane 26 and pivoted down to forty degrees below the horizontal plane 26, resulting in the constant torque hinge 82 maintaining the position of the UV housing 22 at any front position within the sixty-degree front position range. The front position range of the UV housing 22 promotes a distance of separation between the UV lamp 38 and the keypad device 30 within the range of three to seven inches, thereby achieving maximum disinfection of the surface of the keypad device 30 in a minimum time period.

Figure 2C:
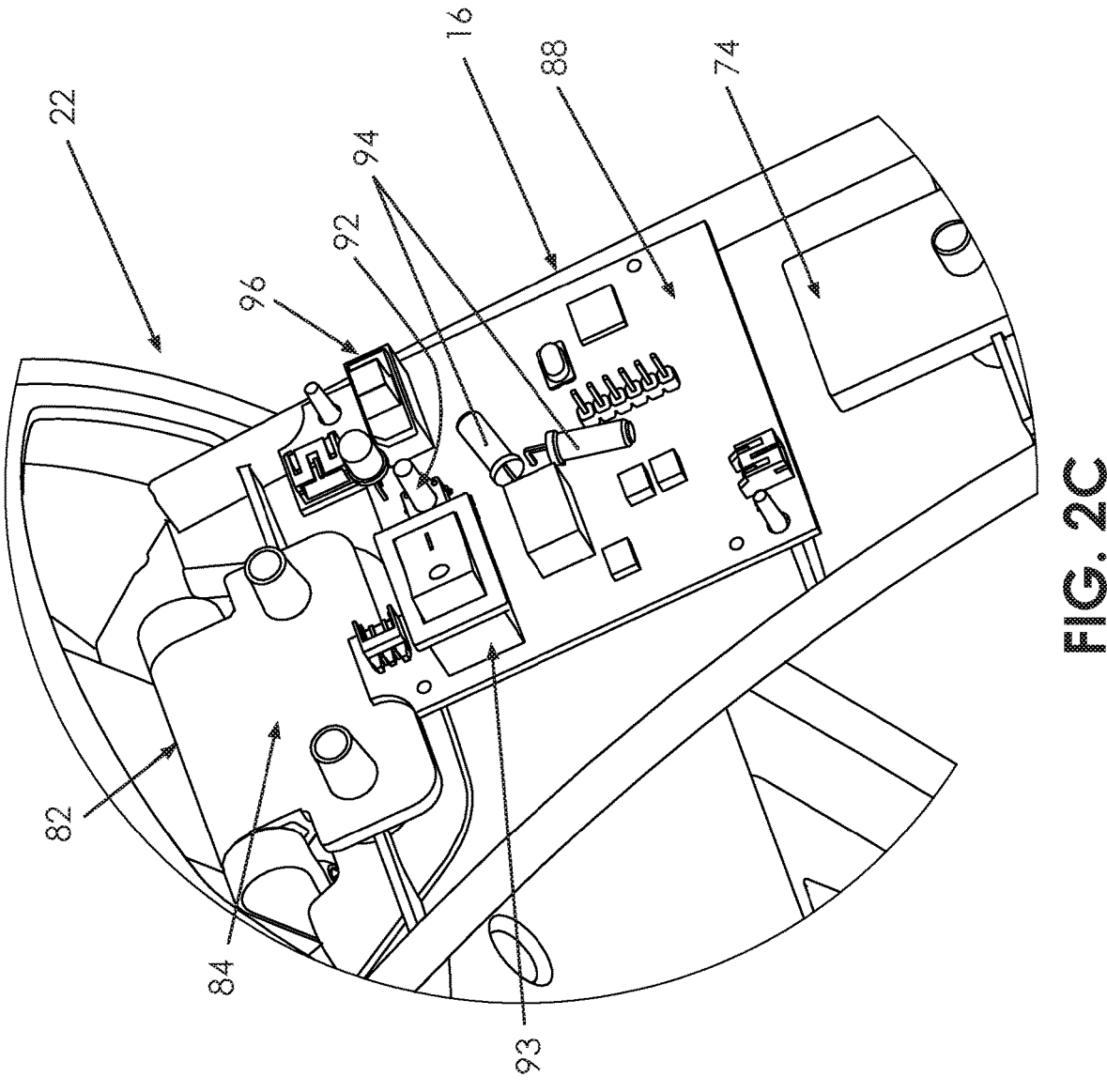
FIG. 2C is a perspective view of the control board depicted in FIG. 2 depicting electrical switches that sense the position of the arm member and energize or de-energize the UV lamp.
Figure 3:
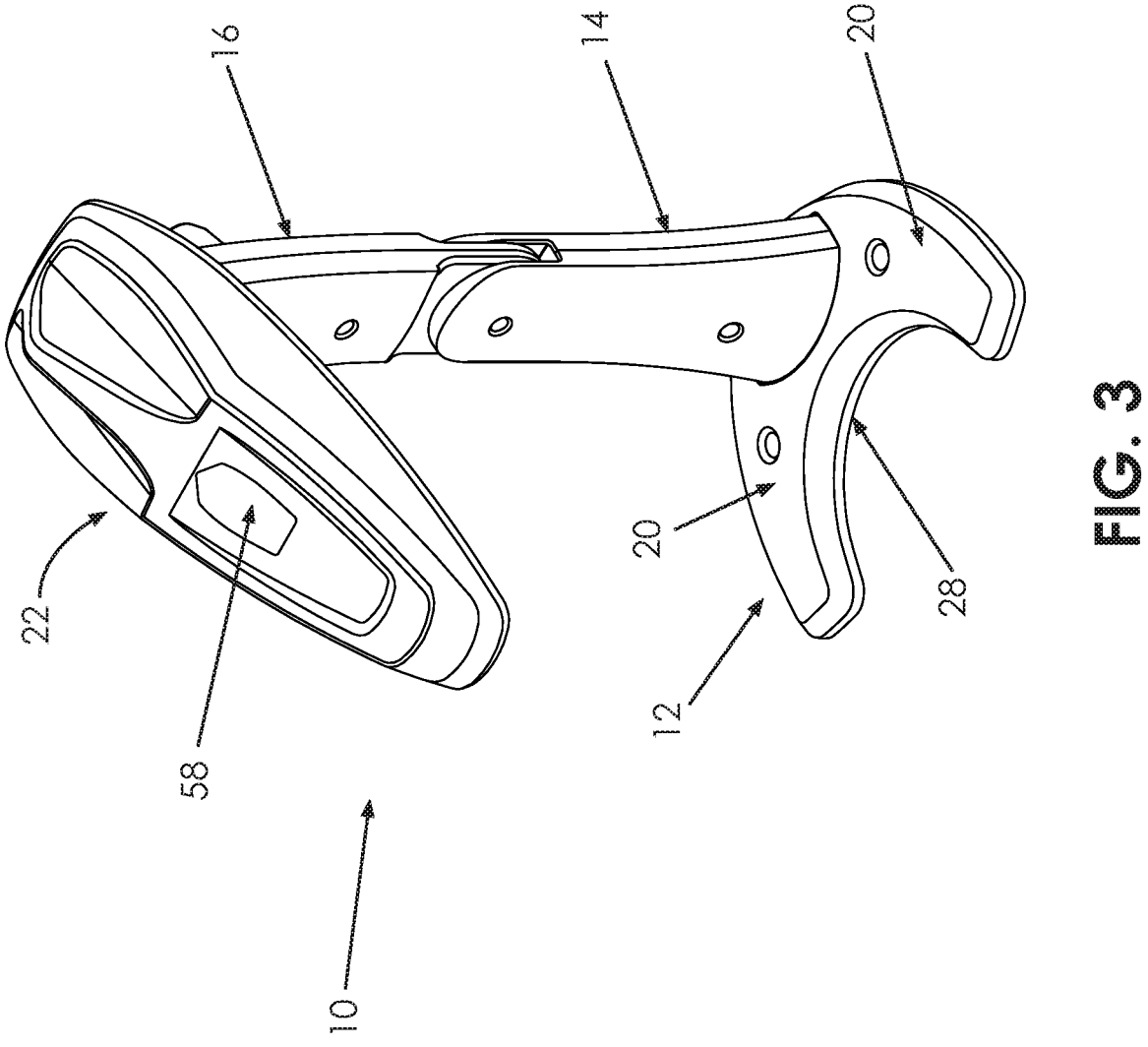
FIG. 3 is a front perspective view of the UV device in FIG. 1.
Figure 4:
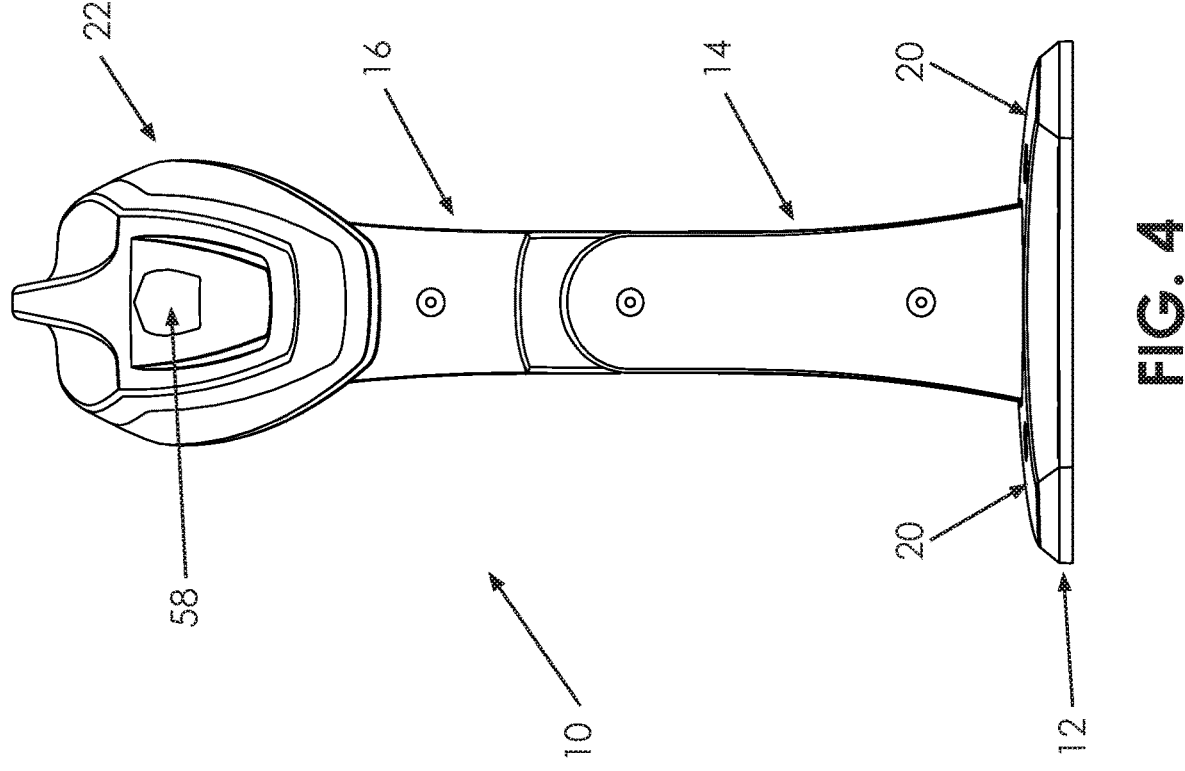
FIG. 4 is a front elevation view of the UV device in FIG. 3.
Figure 5:
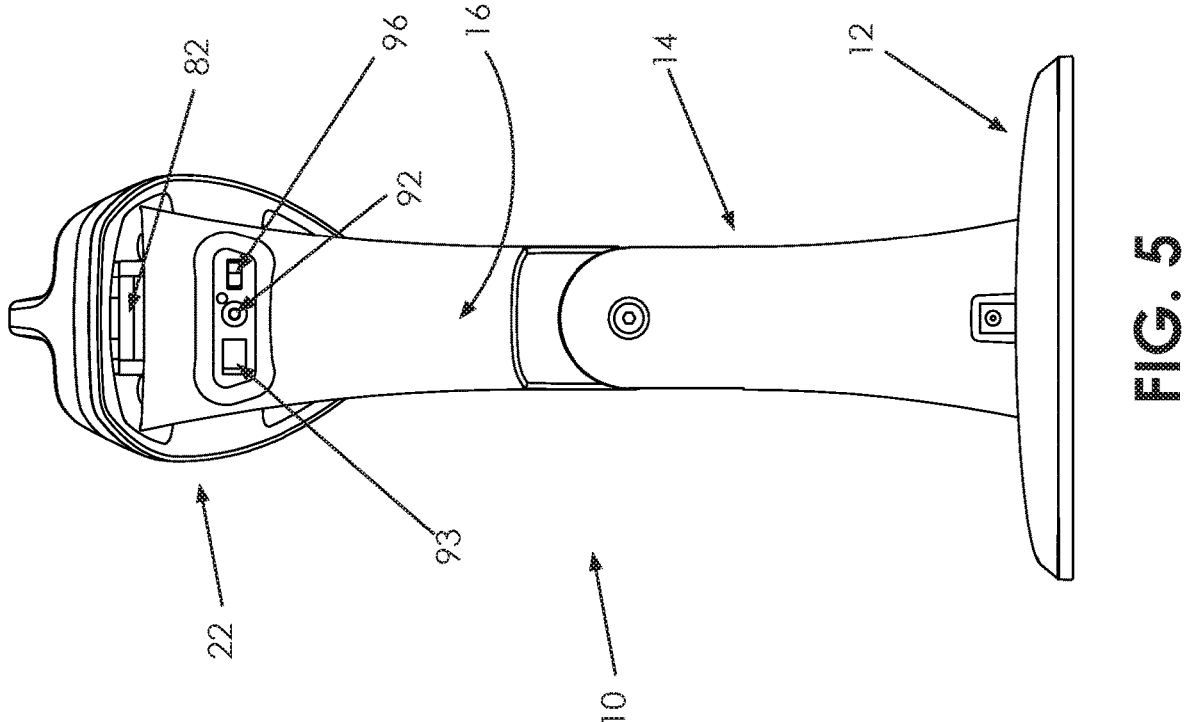
FIG. 5 is a rear elevation view of the UV device in FIG. 3.
Figure 6:
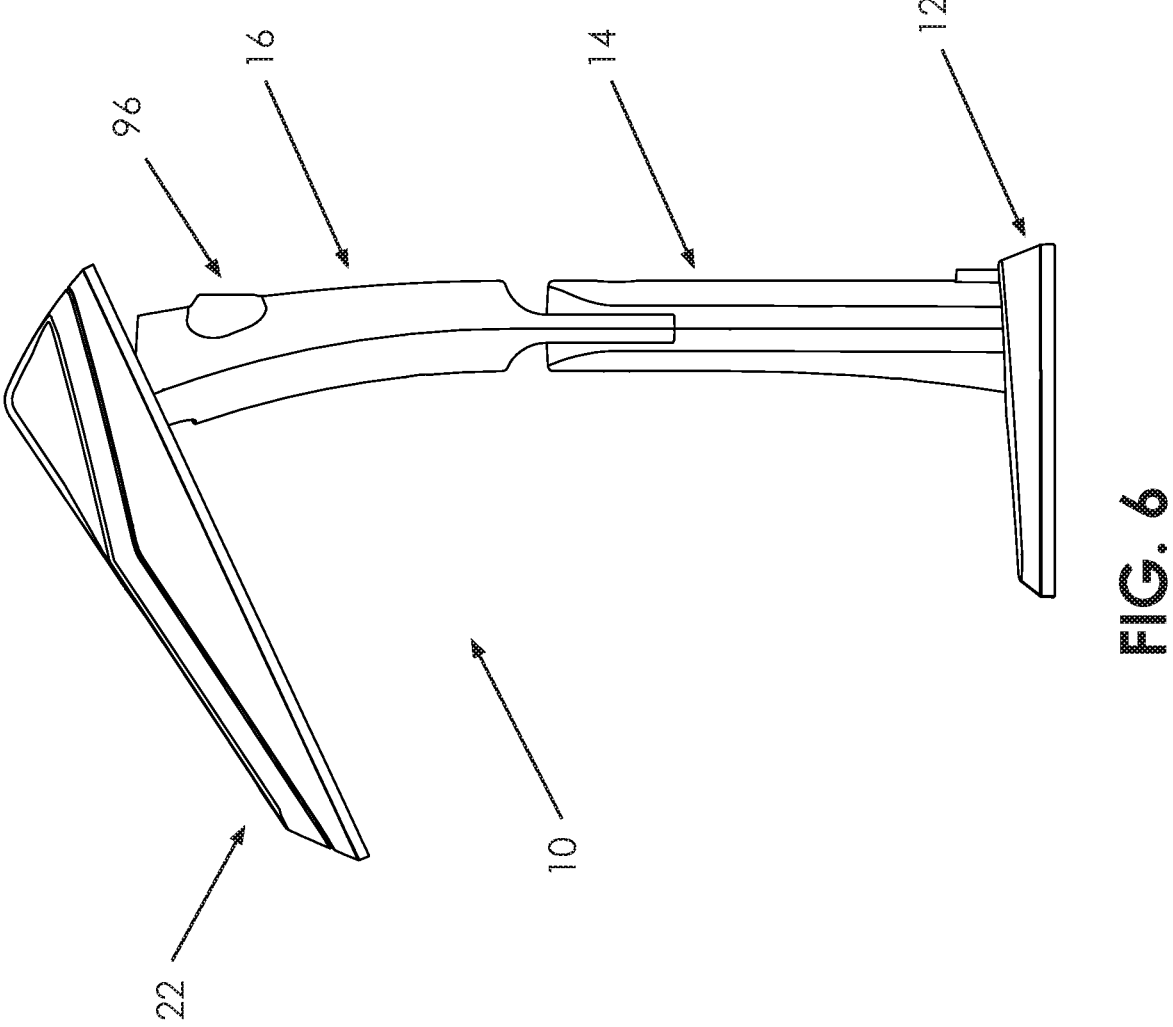
FIG. 6 is a right side elevation view of the UV device in FIG. 3.
Figure 7:
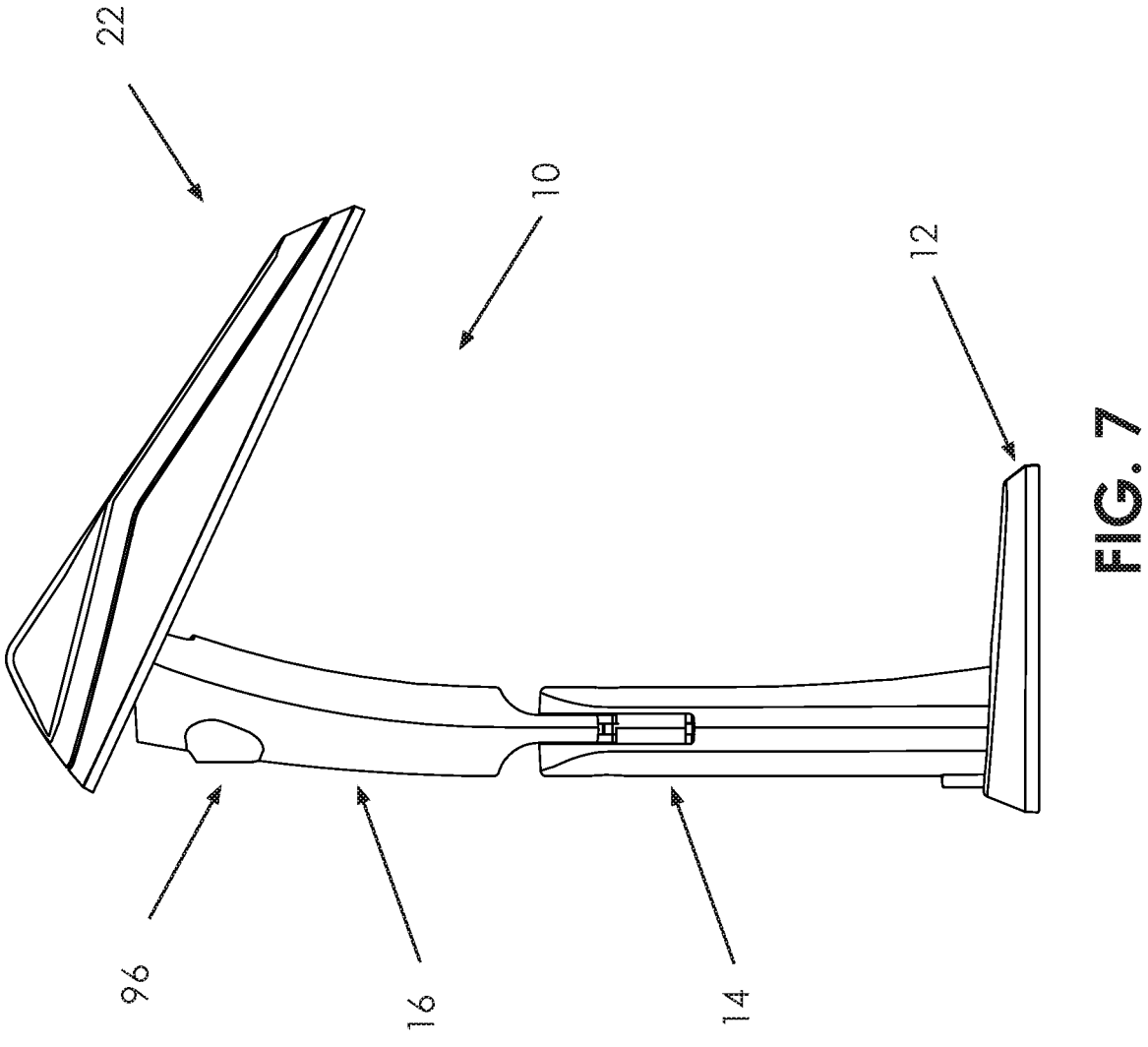
FIG. 7 is a left side elevation view of the UV device in FIG. 3.

Referring FIGS. 2 and 2C, a control board 88 or control member having components and functions well known to those of ordinary skill in the art is detachably secured to an inner wall of the back cover 72 of the arm member 16, whereby, the control board 88 is encased in the arm member 16 and positioned adjacent to and electrically connected to the UV lamp 38 and the colored lights 91 on the LED circuit board 60 behind the display lens 90 and secured to the back upper portion 54 of the arm member 16. The control board 88 electrically energizes and de-energizes the ultraviolet light lamp when the arm member 16 and/or housing 22 are rotated a predetermined distance. The control board 88 includes two redundant electrical switches 94 that sense the vertical and rotated positions of the arm member 16 and are electrically connected to a myriad of electronic components on the control board 88 that cooperate to de-energize and re-energize the UV lamp 38 when the arm member 16 and/or lamp housing 22 is rotated from a vertical position and correspondingly rotated back to a vertical position. The switches 94 are manufactured by ITT C&K and identified via part number RB231X2.

If the UV housing 22 is left in a vertical position after the irradiation cycle is complete, the purple light pulses and fades until the UV lamp housing 22 is rotated to a side position relative to the keypad device 30, and/or until a cycle reset switch 92 (see FIG. 5) electrically connected to the control board 88 is pressed. The colored lights provide an estimate as to the remaining irradiation time, thereby avoiding the user from losing focus on the UV device 10. The pulsating purple light informs the user of the keypad device 30 that the UV lamp 38 is energized and irradiating. After the purple light de-energizes and the decontamination process for the keypad device 30 after the purchaser has removed their credit/debit card, another user can Immediately insert their credit/debit card into the keypad device 30, thereby reducing the time that a purchaser delays using the device 10 for another financial transaction, resulting in more financial transactions in a respective time period.

The UV housing 22 includes the cycle reset switch 92 manufactured by E-Switch (part number TL1105KF160Q) for restating a cycle duration time, an on-off rocker power switch 93 manufactured by E-Switch (part number RA131C1121) (FIG. 5), and a three-position cycle duration switch 96 manufactured by ITTC&K (part number S52328GSNSSW1) (FIG. 5) for selecting one of three cycle duration times for the UV lamp 38 to emit UV light for irradiating the keypad device 30. The switches 92, 93 and 96 are all well known to those of ordinary skill in the art. When the UV housing 22 is vertically adjusted within the three to seven-inch front position range, the cycle duration time for the UV lamp 38 can be correspondingly adjusted from a minimum exposure time for three inches of separation to a maximum exposure time for seven inches of separation.

The UV lamp 38 can be selected from a myriad of light manufacturers, however, for purposes of the present invention, a UV lamp 38 is required that reduces and/or eliminates microbial viruses and pathogens to levels not harmful to humans. Further, the selected UV light member should not be harmful to human skin and eyes. A preferred UV lamp 38 that decontaminates without injuring persons exposed to the UV lamp 38 is a "Far UVC light" having a krypton-chlorine Excimer Lamp that emits monoenergetic UV light at substantially a wavelength of 222 nanometers ("nm"). The preferred UV lamp 38 effectively inactivates a contagious virus but is not cytotoxic or mutagenic to mammalian cells. The preferred UV light member 12 is manufactured by Eden Park and is depicted on the company's website at: https://edenpark.com. The preferred UV lamp 38 decontaminates surfaces engaged by humans, previously engaged by humans or within a predetermined space occupied by humans, whereby, a person or persons exposed to the ultra violet light is not harmed.

The UV Excimer Lamp with a UV wavelength of 222 nanometers includes power ratings of twelve, twenty and three hundred watts. The power rating is determined based upon the distance between the UV lamp 38 and the surface to be decontaminated, the surface area and the time allowed for the surface area to be decontaminated. The preferred use of the present invention is to decontaminate the cover and keys of a credit/debit card keypad 30 terminal on a constant basis ensuring that before, during and after each use the buttons and panel are decontaminated. As an alternative, the UV lamp 38 can be de-energized when a person engages the keypad 30 terminal via a laser break beam sensor (not depicted, but well known to those of ordinary skill in the art), and re-energized after the person's hand disengages the keypad and is removed from the laser beam of the laser break beam sensor, thereby ensuring that the UV light does not engage the person's hand and disinfecting the keypad prior to the next use. The preferred power rating of the UV lamp 38 for decontaminating the keypad 30 is twelve watts with a twelve-volt input to the ballast board 48.

A UV lamp 38 must ultimately be selected to irradiate and destroy a virus of concern. Estimated dosages for destroying Coronavirus' range from 7 mJ/cm2-241 mJ/cm2. UV dosage is calculated by: (dosage=UV light intensity (lamp power and UV frequency)×time) or mJ/(sec)(cm2)×time=mJ/cm2.

The UV germicidal irradiation device 10 of the present invention is can be programmed to have a time value setting (lamp on) based on the distance from the surface to be irradiated (light intensity). The greater the distance between the UV lamp 38 and the surface to be irradiated, the less intense the UV light engulfing the surface.

At 100 cm, the Eden Park UV lamp 38 provides UV light having 5 mj/com2 of UV fluency.

Examples of dosages for time periods follow:
1. 15 seconds, provides dosage of:
    75 mj/cm2 total dosage @ 100 mm (4")
2. 30 seconds, provides dosage of:
    a. 150 mj/cm2 total dosage @100 mm (4")
    b. 90 mj/cm2 total dosage @125 mm (5")
    c. 66 mj/cm2 total dosage @150 mm (6")
3. 60 seconds, provides dosage of:
    a. 250 mj/cm2 total dosage @100 mm (4")
    b. 70 mj/cm2 total dosage @ 175 mm (7')

The foregoing description is for the purpose of illustration only and is not intended to limit the scope of protection accorded this invention. The scope of protection is to be measured by the following claims, which should be interpreted as broadly as the inventive contribution permits.

The invention claimed is:

1. An ultraviolet light germicidal irradiation device for an object comprising:
    a base member having a mounting plate for detachably securing said base member to a selected surface;
    an extension member detachably secured to said base member, said extension member including a bracket plate having a top protrusion portion extending through an aperture in a spring retainer washer and into a bottom portion of a spring engaging and disposed between said spring retainer washer and a cam member, said cam member including a spring retainer portion extending into a top center portion of said spring a distance promoting engagement of a bottom portion of said cam member with a top portion of said spring;
    an arm member rotationally secured to and substantially linearly aligned with said extension member, whereby, a top portion of said arm member is disposed in a position that promotes access to an object to be irradiated with ultraviolet light, said arm member including a cam plate having a lower portion configured to cooperatively engage said cam member, said bottom of said cam member and said spring retainer portion of said cam member cooperating with said top protrusion portion of said bracket plate and said spring retainer washer to capture and compress said spring when rotating said arm member, until a portion of said cam plate engages a cooperating portion of said cam member;
    an ultraviolet light housing secured to said top portion of said arm member; and
    an ultraviolet light lamp disposed inside said ultraviolet light housing, said ultraviolet light lamp emitting an ultraviolet light at a preselected wavelength that destroys a preselected virus when said ultraviolet light housing is in a substantially vertical position, said ultraviolet light lamp automatically de-energized when said arm member is rotated from a vertical position, whereby, said de-energized ultraviolet light lamp promotes access to the object to be irradiated with ultraviolet light, said ultraviolet light lamp being re-energized when said arm member is returned to a vertical position and a reset switch is pressed.

2. The ultraviolet light germicidal irradiation device of claim 1 wherein the de-energizing of said ultraviolet light lamp is controlled by a control board detachably secured in said arm member, said control board includes multiple gyros for de-energizing and re-energizing said ultraviolet light lamp when said arm member is respectively rotated from a vertical position and correspondingly rotated back to a vertical position.

3. The ultraviolet light germicidal irradiation device of claim 2 wherein said ultraviolet light housing is detachable secured to said top portion of said arm member via a constant torque hinge detachably secured to said ultraviolet light housing and said arm member, thereby enabling said ultraviolet light housing to be positioned to maintain upper and lower locations, whereby, a front portion of said ultraviolet light housing has a preselected pivoting range up to twenty degrees above a horizontal plane and down to forty degrees below the horizontal plane, resulting in said constant torque hinge maintaining the position of said front portion of said ultraviolet light housing at any position of said preselected pivoting range, thereby promoting a distance of separation between said ultraviolet light lamp and the object within a range of three to seven inches for achieving maximum disinfection of the surface of the object in a minimum time period.

4. An ultraviolet light device for disinfecting an object comprising:

a base member having a mounting plate for detachably securing said base member to a selected surface;

an extension member detachably and substantially perpendicularly secured to said base member, said extension member including a bracket plate having a top protrusion portion extending through an aperture in a spring retainer washer and into a bottom portion of a spring engaging and disposed between said spring retainer washer and a cam member, said cam member including a spring retainer portion extending into a top center portion of said spring a distance promoting engagement of a bottom portion of said cam member with a top portion of said spring;

an arm member rotationally secured to said extension member, whereby, said arm member is displaced from a substantially linearly aligned position with said extension member to a substantially horizontal position; whereupon, a bottom of said cam member and said spring retainer portion cooperate with said top protrusion portion of said bracket plate and said spring retainer washer to capture and compress said spring until a portion of a cam plate engages a cooperating portion of said cam member;

an ultraviolet light housing secured to a top portion of said arm member; and an ultraviolet light lamp disposed inside said ultraviolet light housing, said ultraviolet light lamp emitting an ultraviolet light at a preselected wavelength when initiated via a control member when said arm member is in a substantially vertical position, said ultraviolet light lamp being de-energized via said control member when said arm member is rotated from a vertical position, whereby, said de-energized ultraviolet light lamp prevents exposure to ultraviolet light generated by said ultraviolet light lamp, said ultraviolet light lamp being re-energized by said control member when said arm member is returned to a substantially vertical position and a reset switch is pressed.

5. An ultraviolet light germicidal irradiation device for an object comprising:

a base member having a mounting plate for detachably securing said base member to a selected surface;

an extension member detachably and substantially perpendicularly secured to said base member, said extension member including a bracket plate having a top protrusion portion extending through an aperture in a spring retainer washer and into a bottom portion of a spring engaging and disposed between said spring retainer washer and a cam member, said cam member including a spring retainer portion extending into a top center portion of said spring a distance promoting engagement of a bottom portion of said cam member with a top portion of said spring;

an arm member rotationally secured to and substantially linearly aligned with said extension member until said arm member is rotated to a position that promotes access to an object irradiated by said ultraviolet light germicidal irradiation device, said arm member including a cam plate having a lower portion configured to cooperatively engage said cam member, whereby upon rotating said arm member, said spring retainer portion and said bottom portion of said cam member cooperate to compress said spring against said spring retainer washer until said cam member is angularly positioned via the axial location of a first retaining pin inserted through said cam member, and the axial location of a second retaining pin engaging said bottom portion of said cam member;

an ultraviolet light housing pivotally secured to said top portion of said arm member, whereby, a front portion of said ultraviolet light housing has a pivoting range from above a horizontal plane to below the horizontal plane;

an ultraviolet light lamp disposed inside said ultraviolet light housing, said ultraviolet light lamp emitting an ultraviolet light at a preselected wavelength; and a control member for electrically energizing and de-energizing said ultraviolet light lamp; whereby, said ultraviolet light lamp is energized when said arm member is linearly aligned with said extension member when required to disinfect an object, said ultraviolet light lamp being de-energized when said arm member is disposed in a rotated position that promotes access to the object, said control member including electrical switches that de-energize and re-energize said ultraviolet light lamp.

6. The ultraviolet light germicidal irradiation device of claim 5 wherein said base member includes a recess for receiving the object, whereby, the object is disposed beneath said ultraviolet light lamp in said ultraviolet light housing when said arm member is substantially linearly aligned with said extension member, the object ultimately receiving ultraviolet light that decontaminates the object when said ultraviolet light lamp is energized.

7. The ultraviolet light germicidal irradiation device of claim 6 wherein said ultraviolet light housing includes a back portion pivotally secured to said top portion of said arm member, whereby, said front portion of said ultraviolet light housing has the pivoting range from at least twenty degrees above the horizontal plane to at least forty degrees below the horizontal plane.

8. The ultraviolet light germicidal irradiation device of claim 7 wherein said extension member and arm member are substantially linearly aligned, whereby, said front portion of said ultraviolet light housing is disposed above the object to be irradiated with ultraviolet light.

9. The ultraviolet light germicidal irradiation device of claim 8 wherein said ultraviolet light housing includes a configuration, when taking a top view of said ultraviolet light germicidal irradiation device, having a longitudinal dimension relatively larger than a lateral dimension of said ultraviolet light housing, thereby distally disposing said ultraviolet light lamp from said arm member.

10. The ultraviolet light germicidal irradiation device of claim 9 wherein said extension member includes front and back covers detachably joined together and to said bracket plate, whereby, said detachably joined front and back covers of said extension member encase said bracket plate.

11. The ultraviolet light germicidal irradiation device of claim 10 wherein said arm member includes front and back covers detachably joined together and to said cam member, whereby, said detachable front and back covers of said arm member encase said cam member and said cam plate.

12. The ultraviolet light germicidal irradiation device of claim 11 wherein said cam plate includes a lower portion configured to cooperatively engage said cam member; whereby, when said arm member is rotated substantially ninety degrees relative to said extension member, said lower portion of said cam plate maintains the rotated position of said arm member via a protrusion portion on said lower portion of said cam plate engaging a tip portion of said cam member; whereupon, first and second retaining pins substantially maintain the position of said cam member when said spring is compressed, thereby limiting the rotational movement of said lower portion of said cam plate upon said tip portion of said cam member, whereby said arm member rotation is limited to ninety degrees and said compressed spring member imparts a force that assists in rotating said arm member to said substantially lineally aligned position with said extension member.

13. The ultraviolet light germicidal irradiation device of claim 12 wherein said extension member and arm member include cooperating longitudinal dimensions, whereby, said ultraviolet light housing is disposed above a keypad device a preselected distance, and said top portion of said arm member is disposed outside the periphery of either side of the keypad device when the arm member is rotated substantially ninety-degrees from a vertical position, thereby promoting relatively easy access to the keyboard device for initiating a financial transaction by inserting a debit/credit card into the keyboard device.

14. The ultraviolet light germicidal irradiation device of claim 5 wherein said ultraviolet light lamp is automatically de-energized when said arm member is rotated from a position substantially lineally aligned with said extension member, whereby, said de-energized ultraviolet light lamp promotes insertion of a credit/debit card into a keypad device, thereby preventing exposure to ultraviolet light generated by said ultraviolet light lamp.

15. The ultraviolet light germicidal irradiation device of claim 14 wherein said ultraviolet light lamp is re-energized when said arm member is returned to said substantially lineally aligned position with said extension member and a reset switch pressed.

16. The ultraviolet light germicidal irradiation device of claim 15 wherein said ultraviolet light housing is detachable secured to said top portion of said arm member via a constant torque hinge detachably secured to said ultraviolet light housing and said arm member, thereby enabling said ultraviolet light housing to be positioned to maintain upper and lower locations, whereby, said front portion of said ultraviolet light housing has said pivot range up to twenty degrees above the horizontal plane and down to forty degrees below the horizontal plane, resulting in said constant torque hinge maintaining the position of said front portion of said ultraviolet light housing at any selected front position within said pivoting range from at least twenty degrees above the horizontal plane to at least forty degrees below the horizontal plane, thereby promoting a distance of separation between said ultraviolet light lamp and the keypad device within the range of three to seven inches for achieving maximum disinfection of the keypad in a minimum time period.

17. The ultraviolet light germicidal irradiation device of claim 16 wherein said arm member, said control member being electrically connected to said ultraviolet light lamp and status indicating lights, said status indicating lights providing a status of an irradiation cycle of said ultraviolet light lamp.

18. The ultraviolet light germicidal irradiation device of claim 17 wherein said status indicating lights include a first LED emitting a green light representing a power on status for said ultraviolet light germicidal irradiation device, a second LED emitting a purple light when said ultraviolet light lamp is energized and irradiating, and a third LED emitting a red light when said ultraviolet light germicidal irradiation device has completed an irradiation cycle and is ready for another financial transaction, said third LED emitting a yellow light when said ultraviolet light germicidal irradiation device experiences a fault condition.

19. The ultraviolet light germicidal irradiation device of claim 18 wherein said second LED emitting a purple light provides fading purple light pulses when said ultraviolet light housing is left in a vertical position after an irradiation cycle is complete, said purple light pulsing and fading until said ultraviolet light lamp is rotated from a substantially vertical position and said reset switch is electrically connected to said control member.

20. The ultraviolet light germicidal irradiation device of claim 5 wherein said ultraviolet light lamp emitting an ultraviolet light at a preselected wavelength of includes an ultraviolet light lamp emitting substantially 222 nm.

* * * * *